(12) United States Patent
Iliffe-Moon et al.

(10) Patent No.: US 11,571,489 B2
(45) Date of Patent: Feb. 7, 2023

(54) METHOD AND APPARATUS FOR PURIFYING AIR OF AN INTERIOR SPACE BY OXIDIZING A PLURALITY OF POLLUTANT COMPOUNDS

(71) Applicant: Bayerische Motoren Werke Aktiengesellschaft, Munich (DE)

(72) Inventors: Etienne Iliffe-Moon, Menlo Park, CA (US); Ann-Christin Gentschev, Munich (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 0 days.

(21) Appl. No.: 15/929,624

(22) Filed: May 13, 2020

(65) Prior Publication Data
US 2021/0353819 A1     Nov. 18, 2021

(51) Int. Cl.
*A61L 9/20*     (2006.01)
(52) U.S. Cl.
CPC .......... *A61L 9/205* (2013.01); *A61L 2209/16* (2013.01)
(58) Field of Classification Search
CPC ............................. A61L 9/205; A61L 2209/16
See application file for complete search history.

(56) References Cited

U.S. PATENT DOCUMENTS

| | | | |
|---|---|---|---|
| 10,363,326 B2 | 7/2019 | Dellock et al. | |
| 10,377,351 B2 * | 8/2019 | Dellock | G06F 3/00 |
| 2012/0070335 A1 * | 3/2012 | Carey | A61L 9/205<br>422/4 |
| 2019/0046680 A1 | 2/2019 | Goswami et al. | |
| 2019/0091738 A1 * | 3/2019 | Chen | B60H 1/00742 |

FOREIGN PATENT DOCUMENTS

| | | |
|---|---|---|
| EP | 0836527 B1 | 8/2003 |
| EP | 2104517 B1 | 1/2012 |
| KR | 20170006346 A | 1/2017 |

OTHER PUBLICATIONS

Buonanno et al. "Germicidal Efficacy and Mammalian Skin Safety of 222-nm UV Light," Radiation Research, 187(4), 493-501, (Feb. 22, 2017) (Year: 2017).*

* cited by examiner

*Primary Examiner* — Timothy C Cleveland
(74) *Attorney, Agent, or Firm* — 2SPL Patent Attorneys PartG mbB; Kieran O'Leary (57) ABSTRACT

Embodiments generally relate to a method for purifying air of an interior space by oxidizing a plurality of pollutant compounds suspended in the air. The method comprises exposing the air of the interior space to a photocatalytic layer, wherein the photocatalytic layer is disposed onto an at least one surface of a porous substrate material located in the interior space, wherein the photocatalytic layer comprises a plurality of photocatalyst particles, and activating the photocatalytic layer with a light source, wherein the activated photocatalytic particles promote a reaction between the pollutant compounds and the air.

16 Claims, 4 Drawing Sheets

METHOD AND APPARATUS FOR PURIFYING AIR OF AN INTERIOR SPACE BY OXIDIZING A PLURALITY OF POLLUTANT COMPOUNDS

FIELD

Embodiments generally relate to a method for purifying air of an interior space by oxidizing a plurality of pollutant compounds suspended in the air. In particular, embodiments relate to a concept for purifying air in a vehicle using a sunshade.

BACKGROUND

Air purification and surface sanitization are increasingly important components in personal and public health. According to the US Environmental Protection Agency (EPA), the average American spends 90% of their time indoors where the levels of indoor air pollutants are often 2 to 5 times higher than outdoor levels. Furthermore, individuals who are most susceptible to the adverse effects of pollution—like the very young, old, and those with certain diseases—spend even more of their time indoors. Additionally, the use of synthetic materials, furnishings, personal care products, pesticides, and household cleaners have increased indoor concentrations of some pollutants.

Many industries, including the automotive industry, have incorporated air purification into their products. Health and wellness issues related to air purification include maintaining or improving the quality of the air, reducing the presence of harmful bacteria or viruses suspended in the air, and deodorizing or controlling the odor of the air. Additionally, these concerns also apply to emerging mobility concepts and products, such as on-demand mobility, car-sharing, car-hailing, or car-pooling. In such instances, multiple users and multiple trips will be made in a day, which may expose drivers or passengers to volatile organic chemicals (VOCs), inorganic compounds, viruses, bacteria, or odors. Hence, there may be a desire for an improved method of air purification in interior spaces.

SUMMARY

Embodiments in the present disclosure relate to methods for purifying air of an interior space by oxidizing a plurality of pollutant compounds suspended in the air. According to an embodiment, a method may comprise exposing the air of the interior space to a photocatalytic layer, wherein the photocatalytic layer is disposed onto at least one surface of a porous substrate material located in the interior space and the photocatalytic layer comprises a plurality of photocatalyst particles. The method further comprises activating the photocatalytic layer with a light source, wherein the activated photocatalytic particles promote a reaction between the pollutant compounds and the air.

Purification is the removal of pollutant compounds from the air in an interior space to improve indoor air quality. Compounds like dust, pollen, pet dander, mold spores, and dust mite feces can act as allergens, triggering allergies in sensitive people. Smoke particles and volatile organic compounds (VOCs) can pose a risk to health. VOCs are numerous, varied, and ubiquitous organic chemicals that have a high vapor pressure at ordinary room temperature. They include both human-made and naturally occurring chemical compounds. VOCs are not acutely toxic, but exposure may have compounding long-term health effects and increases the likelihood of infections or chronic disease.

A photocatalytic layer is a material comprising photocatalyst particles. These particles absorb light—often in the ultraviolet or visible region of the electromagnetic spectrum—to bring them to a higher energy level and provide such energy to reacting substances to make a chemical reaction occur. Photocatalysts are typically made of metal oxide, metal sulfide, oxysulfide, oxynitride, or composites thereof. Photocatalysts may be arranged in unique structures, such as layered, tunnel, and pillared structures. A common photocatalyst is titanium dioxide ($TiO_2$). $TiO_2$ is highly efficient at catalyzing dirt and other pollutant compounds in sunlight. It is also non-toxic, chemically inert in the absence of light, inexpensive, relatively easy to handle, and deposits into thin films. It also is an established household chemical that is used as a pigment in cosmetics, paints, and as a food additive. $TiO_2$ and other common photocatalysts are activated by ultraviolet (UV) light or radiation rather than visible light alone. UV light is electromagnetic radiation with a wavelength from 10 nm (with a corresponding frequency of approximately 30 PHz) to 400 nm (750 THz). It is shorter than that of visible light but longer than X-rays. UV radiation is present in sunlight and constitutes about 10% of the total electromagnetic radiation output from the Sun.

The substrate material may be porous or breathable. Porous substrates have minute interstices or gaps through which liquid or air may pass. The disposition of the layer onto the substrate material should not drastically alter or change the material's absorption ability for air to pass through freely. By allowing air to pass through the substrate material, air can more freely circulate through the interior allowing more pollutant compounds to encounter the photocatalytic layer. Additionally, the porous nature of the material may allow for the photocatalytic layer to be disposed over a greater surface area increasing the possible rate of purification.

Air purification and surface sanitization of an interior space using photocatalyst particles create free radicals on the surface or near-surface of the substrate material. These radicals act on molecular groups of the pollutant compounds that are on the surface of the substrate material or airborne (i.e. in the cabin air). These pollutant compounds may include volatile organic compounds (VOCs) or inorganic compounds. The radicals generated by the oxidization reaction may include hydroxyl radicals, superoxide radicals, or other radicals containing a reactive oxygen species. Importantly, the radicals are surface-bound, not free, meaning the activated radical group is part of a molecule being chemically bound to the surface of the substrate. This method may have the benefit of not producing ozone or other harmful reaction products. As the radicals are bound to the surface of the substrate, this also means that the surface may be sanitized or disinfected. Finally, the photocatalytic layer may be useful for the elimination of odors or malodors, such as those from general use or off-gassing of materials or surfaces. Pollutant compounds may also include biological components or organisms (e.g. viruses, bacteria, fungi, etc.). The radicals on the surface or near-surface of the substrate material may be toxic to pollutant compounds such as bacteria or mold and may interfere with their lifecycle or reproduction.

In another embodiment, the photocatalytic layer is non-reactive with the substrate material. When activated the photocatalyst and any radicals generated do not react or interact with substrate material and any other coatings, chemical applications, or other materials applied to it. This reduces the degradation or decomposition of the substrate material preserving its characteristics (e.g. color and texture), structure, and overall lifespan.

In a further embodiment, the reaction between the pollutant compounds and the air is a photoelectrochemical reaction. Photoelectrochemical oxidation (PeCO) is a special case of photochemical oxidation (PCO) that occurs in electrochemical systems such as semiconductors. PCO entails the generation of radical species that enable oxidation reactions, with or without the electrochemical interactions involved in semiconductor-catalyzed systems. PECO catalysts, such as semiconductors, may require less energy to promote a catalytic oxidation reaction thus producing radicals using the lower-energy visible light radiation rather than in the higher-energy UV radiation. PeCO catalysts may produce hydroxyl radicals in the presence of water molecules ($H_2O$) in the air. These hydroxyl free radicals are extremely potent oxidizers, which oxidize organics and microorganisms in the air to form carbon dioxide ($CO_2$) and water and trace minerals.

In an embodiment, the method may further comprise suspending the substrate material in the interior space. Suspending the substrate material or otherwise orientating it so that it has contact with the air on all sides may increase the efficiency of the method by allowing for more air to pass through the substrate. This would increase the surface area of the photocatalytic layer as well as the rate at which pollutant compounds are oxidized. Suspending the substrate material may also give it better exposure to sunlight as the light source.

As used in the interior of a vehicle, the substrate material may be an interior surface or panel of the vehicle (e.g. seats, headrests, handles, steering wheel, displays, buttons, switches, etc.). Structures like a seat cover, a sunshade, a sunroof shade, a parcel shelf, and a trunk cover may receive greater exposure to sunlight. This may increase their effectiveness through passive activation by sunlight as well as exposure to the circulation of the interior or cabin air. Additionally, these applications may not need forced air circulation (e.g. from a fan) and may use the natural convection airflow from sunlight heating those cabin surfaces. Passive activation of the photocatalysts is energy efficient, silent (i.e. no noise from fans), and does not require consumables (e.g. filters, disinfectants, etc.). By remaining passive or semi-passive, the purification may be ambient in that it is not directly observed or noticed by inhabitants. It may also allow the interior space to be used by inhabitants without risk to their exposure to free radicals.

The interior space of the method may be the cabin of a vehicle. Of used in a vehicle, the passive purification may be lightweight and use little-to-no energy, preserving the range of an electric vehicle.

The porous substrate material used in the method may include a woven fabric and/or a non-woven fabric. The use of fabric allows for air to pass through the material and circulate more freely through the interior space. Porous fabrics, such as woven or knitted performance fabrics or meshes (e.g. with bi-axial or tri-axial structures), are breathable and allow air to freely pass through, due to either a loosely woven texture or structure produced from a synthetic or natural yarn. Non-woven are generally fabric-like materials made from staple fiber and long fibers, bonded together by chemical, mechanical, heat or solvent treatment. Non-woven fabrics are typically flat or tufted porous sheets. The term is used in the textile manufacturing industry to denote fabrics, such as felt, which are neither woven nor knitted.

The porous substrate material of the method may include a ceramic, a metal, and a polymer. Non-porous materials retard fluid absorption, meaning air is not able to pass freely through tightly bonded non-porous materials. However, hard materials may be porous by their nature or by their construction. For example, although both granite and sandstone are natural stones or rocks sunstone is known to be very porous, especially compared to granite. Likewise, raw concrete is much more porous than concrete that is polished or sealed with a water-repellent substance. External treatment of fabric can drastically alter or change a material's absorption ability for air to pass through freely. Therefore, the substance material should be kept porous to retain its increased purification effects.

In another embodiment, the light source of the method may be an artificial source of light. The artificial source of light may include any range of wavelengths across the UV light spectrum. The UV may be from an electric source of UV (e.g. UV LEDs). The artificial source of UV light can specifically emit UV-A, UV-B, or UV-C radiation and can be attuned to the catalyst.

In a further embodiment, the light source may emit or radiate light consisting essentially of UV-A, UV-B light, or far-UV-C light. UV radiation can be harmful to humans, mammals, and other animals in excessive quantities. While UV radiation does not cause an immediate reaction, accumulative exposure may cause harm. Therefore, employing the method above may include limiting exposure of occupants or inhabitants of the interior space to UV light. This is generally true with UV-C radiation—the highest-energy, most-dangerous type of ultraviolet radiation—that may cause mutagenic, carcinogenic, or other adverse effects. Generally, UV-C radiation can penetrate mammalian skin to harm DNA and living cells; however, it is typically blocked by the atmosphere and is not a factor for humans or other animals (such as pets) in direct sunlight. Still, humans, mammals, and other animals may be exposed to it through artificial light sources. UV-C radiation is also harmful to materials and can degrade the materials found in a vehicle interior (e.g. leather, wood, fabrics, plastics, rubbers, paint, surface treatments or coatings, etc.). Therefore, harmful exposure should be substantially avoided. Nevertheless, UV-C radiation may be useful to activate the photocatalytic particles as well as provide secondary disinfectant effects in the interior space when no living organism is present because it is the radiation with the highest-energy. Furthermore, certain wavelengths of UV-C light—namely far-UV-C light generated by filtered excimer lamps emitting in the 207 to 222 nm wavelength range—may penetrate and deactivate or destroy bacteria and viruses without penetrating human or other mammalian skin. This is because, due to its strong absorbance in biological materials, far-UV-C light does not have sufficient range to penetrate the outer layer on the surface of human skin, nor the outer tear layer on the outer surface of the eye, neither of which contain living cells. Yet, because bacteria and viruses are typically of micron or smaller dimensions, far-UV-C light may still efficiently penetrate and deactivate them. (Welch, D., Buonanno, M., Grilj, V. et al. Far-UVC light: A New Tool to Control the Spread of Airborne-Mediated Microbial Diseases. Sci Rep 8, 2752 (2018).)

In an embodiment of the method, the light source may be a hybrid between a natural light source and an artificial light source. For example, the method could be driven by natural sunlight during daytime and supplemented at nighttime or daytime by UV LEDs. For example, the method could further include sensing the level of natural UV light and adjust the intensity or brightness of the UV LED source automatically. This would allow for sustained purification of the air rather at all hours and in all lighting or UV radiation conditions.

Another embodiment of the method may further comprise determining occupancy information on the interior space, and wherein activating the light source is determined by the occupancy information, wherein the light source's emissions consists essentially of UV-C light. Because UV-C radiation is the highest-energy form of UV light it is also the most effective at activating the photocatalytic layer. However, UV-C's potential for harming humans, animals (such as pets), or any other biological occupants means that UV-C light may be restricted when occupants are present in the interior space. Harmful UV-C light may also be used when occupants are appropriately shielded from the negative effects of UV-C radiation. Determining occupancy information may include determining the absence of an occupant, meaning a human, animal, or another living organism. It may also mean determining that the occupants of the interspace are properly protected or shielded from the artificial light source so that they are not exposed to significant harm. Determining occupancy information may be done by any means, such as through seat sensors, visual or infrared cameras, steering wheel hand detection, door sensors, motion sensors, or any other means.

As an example, if an artificial light source emitting UV-C light is directed at the photocatalytic layer—or otherwise shielded and contained—in a way that no light affects the occupant of the space it may be safe to use when an occupant is also in the interior space. Otherwise, the light source is not activated to protect the occupant. One example may be if the photocatalytic layer is disposed on the upper surface of a shade for a sunroof and the artificial light source is directed to that upper surface when the shade is closed or otherwise shields the light source's emissions from the occupant or occupants. This may allow UV-C or other light that would be otherwise harmful to the occupant to be safely used while the occupant is in the interior space.

In another embodiment, the method may further comprise inducing airflow in the interior space. Inducing airflow may comprise forcing airflow using at least one of the group of a fan and a heating, ventilation, and air conditioning (HVAC) system. This may allow increased circulation and exposure of the interior air to the photocatalytic layer thereby increasing the purification of the interior space.

The method may further comprise communicating with a vehicle processor to adjusting a system of the vehicle. By integrating with vehicle systems, the method may control the motion or position of a sunshade thereby adjusting the amount of external light activating the photocatalytic layer. It may also coordinate functions of the vehicle for purification, such as coordination of functions between shading sunlight and purification functions. If the substrate material is operating as a cleansable sunshade and is affixed to a cleansing retractor the method may automatically roll back the sunshade to cleanse it. For example, through the rolling action (bending fabric, scrubbing with brushes or brush strip, etc.). Additionally, if in communication with a climate system, the method may adjust the airflow for circulation. It may also sense and adjust the temperate of the cabin of the vehicle. This may be done through airflow or active HVAC cooling/heating to optimized purification. The method may also activate the recirculate function of an HVAC system. Activating the recirculation function may maximize purification cleansing (i.e. pollutants and/or odors). The method may also communicate with a user interface of the vehicle. This allows for a user to interact and communicate with the method (e.g. control, submit feedback, see status information, options, settings, maintenance, etc.)

The method may further comprise receiving information from a vehicle's processor. This information may include information from an occupancy sensor. Understanding if a vehicle is occupied the method may avoid harming or exposing to harm a living organism. The method may also communicate with door and window sensors to open, close, and lock either. This could be coordination with a purification cycle where the method turns turning lights (e.g. ambient and/or UV) on or off, as well as airflow on or off to maximize purification depending on interior conditions.

Additionally, the method may control lighting, such as ambient lighting to indicate purification or cleansing, and create an experience around the purification feature. The method may also control audio to indicate purification or cleansing (e.g. message start or end of cycle and purification activity).

By communicating with vehicle systems, the method may limit exposure to humans and pets by only running purification systems when the vehicle is unoccupied, locked, parked, or at specific times of the day or night.

In another embodiment, the method may further comprise cleansing the photocatalytic layer. As pollutants oxidize and other debris (such as dust or dried liquids) contaminate the photocatalytic layer it may become less effective. Cleansing the photocatalytic layer may be accomplished by washing, brushing, or otherwise removing the pollutants or materials from the photocatalytic layer. By removing these materials, the layer may oxidize pollutants with increased efficiency compared to a photocatalytic layer with pollutants or other debris interfering with the oxidization process. Cleansing of the photocatalytic layer may be done in conjunction with other systems. For example, in a vehicle the photocatalytic layer may be cleansed with an occupant of the vehicle is determined to be absent to minimize the chances that the occupant is affected, disrupted, or distracted by the cleansing. The cleansing may also be done in conjunction with an HVAC system. For example, cleansing may agitate the photocatalytic layer, thereby introducing the oxidized pollutants into the air to be removed from the interior space by an HVAC system with a filter. This has the benefit of reducing the energy consumption of the HVAC system because it may only operate to remove the compounds during or after the agitation of the photocatalytic layer rather than continuously.

In an embodiment, there may be an apparatus for purifying air of an interior space that oxidizes a plurality of pollutant compounds suspended in the air. The apparatus may comprise a substrate material having a photocatalytic layer disposed on at least one surface of the substrate material, wherein the photocatalytic layer comprises a plurality of photocatalyst particles and wherein a light source activates the photocatalytic particles to promote a reaction between the pollutant compounds and the air.

Interior spaces typically recirculate some air, which has been shown to lead to a higher risk of infection during outbreaks, as contaminated air in one area is circulated to other parts of the space, vehicle, or building. When it is very cold or very hot, the air of the interior space may be completely recirculated, increasing the risk or spread of disease or infection. The apparatus can reduce the level of risk by increasing the existing purification level of the interior space passively, with minimal or no energy required.

The apparatus may further comprise an artificial light source, wherein the light source activates the photocatalytic layer. The artificial light source may be any light source (e.g. light-emitting diodes (LEDs)) located exterior to the substrate material. For example, in a vehicle, the lights may be located on the exterior side of a substrate material acting as a sunshade between the sunroof glass and the sunshade. The artificial light source would then be shining into the air cavity between the sunroof glass and fabric. This would protect any inhabitants of the vehicle from being exposed to UV radiation while still activating the photocatalytic layer of the substrate material. Furthermore, the artificial light source could be positioned or directed to reflect UV light off the sunroof glass. This would enable the sunroof glass to be used to refract or guide light across the entire surface of the fabric. Optionally, the sunroof glass can be coated with a UV or light-reflective coating or film. This film would aid with the refraction of the light on the glass as well as protect those outside the vehicle from the UV radiation.

In another embodiment, the apparatus is removable and replaceable. This allows the apparatus to be removed for cleaning, replacement, or refurbishment to maintain the effectiveness of the apparatus and its photocatalytic layer.

In an embodiment, the apparatus may further comprise a cleanser for the photocatalytic layer. As pollutants oxidize and other debris (such as dust or dried liquids) contaminate the photocatalytic layer it may become less effective. Cleansing the photocatalytic layer may be accomplished by washing, brushing, or otherwise removing the pollutants or materials from the photocatalytic layer. By removing these materials, the layer may oxidize pollutants with increased efficiency compared to a photocatalytic layer with pollutants or other debris interfering with the oxidization process. For example, the substrate material may be part of a retractable sunshade, whereby the retraction of the sunshade causes brushes to pass over the photocatalytic layer removing the pollutants and other debris for collection or disposal. The cleanser may automatically pass over the photocatalytic layer with brushes and or a suction device such as a vacuum. Another example of the cleanser may be a device that coats the photocatalytic layer with a liquid, such as water, to wash the pollutants or other debris from the layer to be safely disposed.

In an embodiment, there may be a sunshade for purifying air of an interior space of a vehicle that oxidizes a plurality of pollutant compounds suspended in the air. The sunshade may comprise a substrate material having a photocatalytic layer disposed on at least one surface of the substrate material, wherein the photocatalytic layer comprises a plurality of photocatalyst particles and wherein a light source activates the photocatalytic particles to promote a reaction between the pollutant compounds and the air. The combination of purification and a sunshade provides a mutual benefit if shading the occupants from harmful UV light, whilst harvesting the UV light for purification.

A sunshade is any object or structure that is used as protection from sunlight. In a vehicle, it is typically used as a covering for windows such as a covering for a sunroof. In a further embodiment, a cleansing retractor may be affixed to the sunshade. The cleansing retractor may comprise a housing that substantially contains the sunshade when retracted and brushes affixed to the housing and adjacent to the photocatalytic layer, wherein the brushes cleanse the sunshade of a byproduct of the pollutant compounds as the sunshade retracts into the housing. Cleansing the sunshade by brushing or removing materials from its surface allows for any oxidized compounds or other dirt and grime to be detached from the sunshade and removed. This allows for more surface area of the photocatalytic layer to be exposed and thus more pollutant compounds to be oxidized.

BRIEF DESCRIPTION OF THE DRAWINGS

Some embodiments of apparatuses and systems will be described in the following only by way of example and with reference to the accompanying figures, in which.

DETAILED DESCRIPTION

Various embodiments will now be described more fully with reference to the accompanying drawings in which some embodiments are illustrated. The thicknesses of lines, layers, and/or regions in the figures may be exaggerated for clarity.

Accordingly, while further embodiments are capable of various modifications and alternative forms, some particular embodiments thereof are shown in the figures and will subsequently be described in detail. However, this detailed description does not limit further embodiments to the particular forms described. Further embodiments may cover all modifications, equivalents, and alternatives falling within the scope of the disclosure. Same or like numbers refer to like or similar elements throughout the description of the figures, which may be implemented identically or in modified form when compared to one another while providing for the same or similar functionality.

It will be understood that when an element is referred to as being "connected" or "coupled" to another element, the elements may be directly connected or coupled via one or more intervening elements. If two elements A and B are combined using an "or", this is to be understood to disclose all possible combinations (i.e. only A, only B, as well as A and B) if not explicitly or implicitly defined otherwise. An alternative wording for the same combinations is "at least one of A and B" or "A and/or B". The same applies, mutatis mutandis, for combinations of more than two elements.

The terminology used herein for the purpose of describing particular embodiments is not intended to be limiting for further embodiments. Whenever a singular form such as "a," "an" and "the" is used and using only a single element is neither explicitly or implicitly defined as being mandatory, further embodiments may also use plural elements to implement the same functionality. Likewise, when a functionality is subsequently described as being implemented using multiple elements, further embodiments may implement the same functionality using a single element or processing entity. It will be further understood that the terms "comprises," "comprising," "includes" and/or "including," when used specify the presence of the stated features, integers, steps, operations, processes, acts, elements, and/or components but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the embodiments belong.

Figure 1:
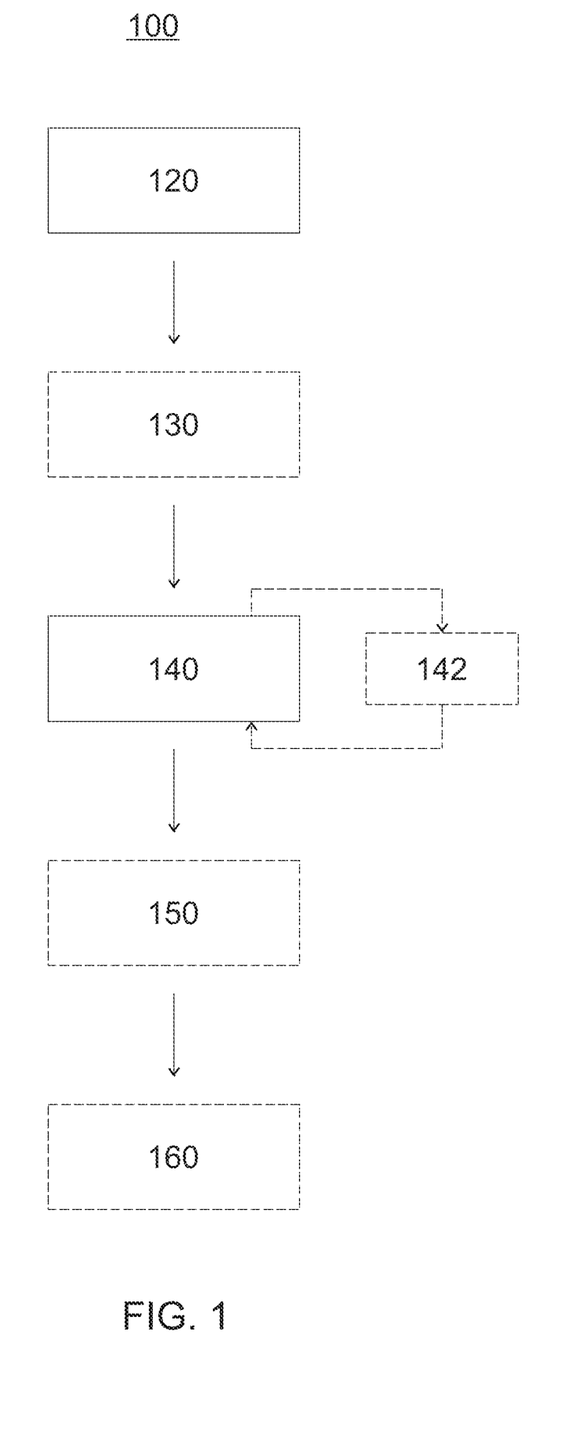
FIG. 1 shows a block diagram of an embodiment of a method for purifying air of an interior space by oxidizing a plurality of pollutant compounds suspended in the air.

FIG. 1 shows a block diagram of an embodiment of a method 100 for purifying air of an interior space by oxidizing a plurality of pollutant compounds suspended in the air. The method comprises exposing 120 the air of the interior space to a photocatalytic layer, wherein the photocatalytic layer is disposed onto an at least one surface of a porous substrate material located in the interior space, wherein the photocatalytic layer comprises a plurality of photocatalyst particles. The method further comprises activating 140 the photocatalytic layer with a light source, wherein the activated photocatalytic particles promote a reaction between the pollutant compounds and the air.

Disposing a photocatalytic layer may be done either pre or post creation of the substrate material. The fibers or yarn of a substrate material may be coated before weaving into a fabric or after the fabric is woven. Woven fabric may be loosely or tightly woven. Looser woven fabrics have greater permeability to air and light. A porous substrate material that is a mesh may allow for air and light permeability and to increase the active surface area for purification.

Exposing 120 a photocatalytic layer may be done by installing the substrate material in the interior space. This may be done by placing a substrate material with the photocatalytic layer in the interior space, such as by placing or adding a sunshade, trunk cover, or other accessory comprising the substrate material and photocatalytic layer. The photocatalytic layer may also be disposed on an existing substrate in the interior space, such as an interior panel, steering wheel, seat cover, or other substrate material in the cabin of a vehicle. Once a photocatalytic layer is disposed on a substrate material either in the interior space or later introduced into the interior space the air of the interior space is then exposed to the photocatalytic layer.

Activating 140 the photocatalytic layer with a light source may be done with natural light from the Sun. The heating effect from the Sun may act to regenerate the photocatalytic material because photocatalytic materials can become poisoned over time by pollutants.

Photocatalyst particles may be heterogeneous, meaning the catalyst is in a different phase from the reactants. A photocatalyst may be any catalysts that react to light, including TiO2, which is generally activated by UV light as well as catalysts activated by visible light, such as tungsten trioxide (WO3), silver phosphate (Ag3PO4), bismuth vanadium oxide (BiVO4), or graphite carbon nitride (g-C3N4). A porous substrate may refer to any permeable, penetrable, pervious, car absorbent, spongy, honeycombed, cellular, or porous material on to which the photocatalytic layer may be disposed.

The photocatalytic layer may be non-reactive with the substrate material. The reaction between the pollutant compounds and the air may be photoelectrochemical.

Optionally, the method may comprise suspending 130 the substrate material in the interior space. Optional components or steps are illustrated using dotted lines. Suspending the substrate may be done by any method, including by hooks, fasteners including hook and loop fasteners, suction, adhesion, and similar methods.

The substrate material may comprise at least one of the group of an interior panel of the vehicle, a seat cover, a sunshade, a sunroof shade, a parcel shelf, and a trunk cover. The interior space of the method may be the cabin of a vehicle. The porous substrate material used in the method may include at least one of the group of a woven fabric and a non-woven fabric. The porous substrate material of the method may include at least one of the group of a ceramic, a metal, a polymer, and a natural or synthetic fiber. Natural materials (such as cotton, silk, and wool) are made of animal or plant-based fibers. Synthetic fibers are man-made and produced entirely from chemicals to create materials like polyester, rayon, acrylic, and many others. The light source of the method may be an artificial source of light. The light source may consist essentially of UV-A, UV-B, or far-UV-C light.

Optionally, the light source may be a hybrid between a natural light source and an artificial light source, wherein the method further comprises augmenting 142 the natural light source with the artificial light source to continue the activation of the photocatalysts.

Optionally, the method may further comprise inducing 150 airflow in the interior space. The method may further comprise communicating 160 with a vehicle processor to adjusting a system of the vehicle.

Figure 2A:
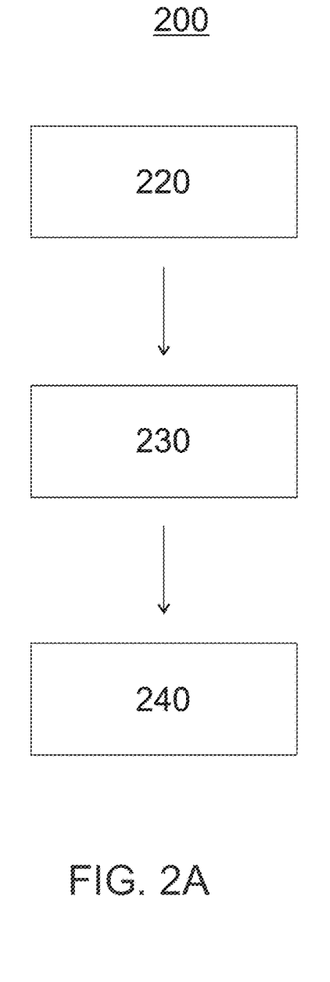
FIG. 2A shows a block diagram of an embodiment of the method further comprising determining occupancy information on the interior space.

FIG. 2A shows a block diagram of an embodiment of a method 200 for purifying air of an interior space by oxidizing a plurality of pollutant compounds suspended in the air. The method comprises exposing 220 the air of the interior space to a photocatalytic layer, wherein the photocatalytic layer is disposed onto an at least one surface of a porous substrate material located in the interior space, wherein the photocatalytic layer comprises a plurality of photocatalyst particles. The method further comprises determining 230 occupancy information on the interior space. The method then comprises activating 240 the photocatalytic layer with a light source as determined by the occupancy information, wherein the light source's emissions consists essentially of UV-C light, and wherein the activated photocatalytic particles promote a reaction between the pollutant compounds and the air.

Figure 2B:
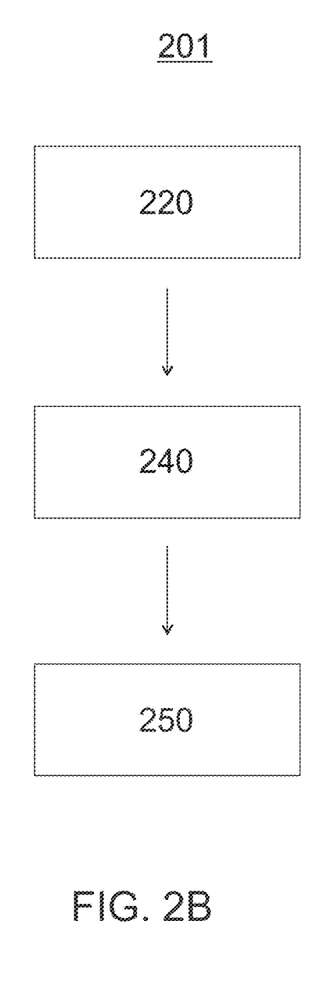
FIG. 2B shows a block diagram of an embodiment of the method further comprising cleansing a photocatalytic layer.

FIG. 2B shows a block diagram of an embodiment of a method 201 for purifying air of an interior space by oxidizing a plurality of pollutant compounds suspended in the air. The method comprises exposing 220 the air of the interior space to a photocatalytic layer, wherein the photocatalytic layer is disposed onto an at least one surface of a porous substrate material located in the interior space, wherein the photocatalytic layer comprises a plurality of photocatalyst particles. The method then comprises activating 240 the photocatalytic layer with a light source. The method further comprises cleansing 250 the photocatalytic layer. Cleansing of the photocatalytic layer may be done in conjunction with other steps. For example, cleansing may be determined by occupancy information to minimize the chances that the occupant is affected, disrupted, or distracted by the cleansing. The cleansing may also be in conjunction with operating or inducing airflow with an HVAC or other air purification system. For example, cleansing may agitate the photocatalytic layer, thereby introducing the oxidized pollutants into the air to be removed from the interior space by an HVAC system with a filter. This has the benefit of reducing the energy consumption of the HVAC system because it may only operate to remove the compounds during or after the agitation of the photocatalytic layer rather than continuously.

Figure 3:
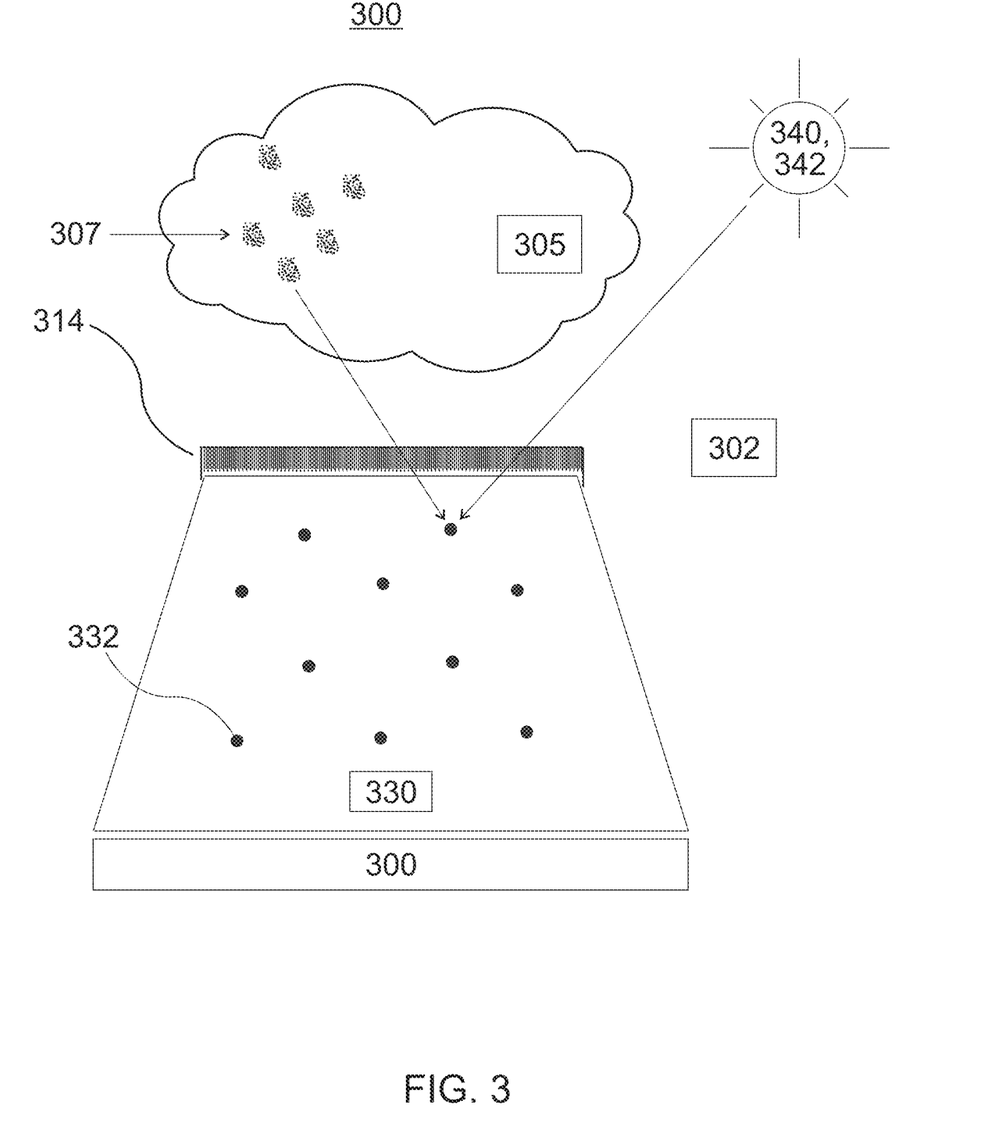
FIG. 3 shows a cross-section of an embodiment of an apparatus for purifying air of an interior space.

FIG. 3 shows a cross-section of an apparatus 300 for purifying air 305 of an interior space 302 that oxidizes a plurality of pollutant compounds 307 suspended in the air. The apparatus 300 comprises a substrate material 320 having a photocatalytic layer 330 disposed on an at least one surface of the substrate material, wherein the photocatalytic layer comprises a plurality of photocatalyst particles 332 and wherein a light source 340 activates the photocatalytic particles 332 to promote a reaction between the pollutant compounds and the air.

The light source may be characterized by an artificial light source 342, wherein the light source activates the photocatalytic layer 330.

The apparatus 300 may be replaceable. The term replaceable means that the apparatus 300 may be conveniently added to or removed from the interior space 302 according to the user's needs. A replaceable apparatus 300 may be interchanged with a different apparatus 300 (e.g. comprising a different photocatalytic layer 330 or different embodiments as described in this application). A replaceable apparatus allows for a new or refurbished apparatus to be used if the original becomes polluted. A different apparatus 300 added to the system may serve a different function depending on its photocatalytic layer or configuration. Further, a producer of replaceable apparatuses 300 may be able to tailor several different versions of the apparatus 300 to provide a curated purification experience to the user. Each replaceable apparatus 300 may also comprise a method of identification so that when it is removably inserted into the interior 302 it can be identified. Additionally, replaceable nature of the apparatus, it is possible for a user to purchase an interior 302 such as a vehicle without an apparatus 300 if it does not meet their present needs and then add the apparatus 300 to the interior 302 when it better suits the user.

The apparatus 300 may further comprise a cleanser 314 for the photocatalytic layer. A cleanser 314 may be any device or apparatus that removes oxidized pollutants from the photocatalytic layer 330. A cleanser may be operated manually or automatically. It may include scrubbers, squeegees, or other tools with a flat blade, sponges, and microfiber cloths. It may also include suction or washing components that loosen or remove the compounds with air pressure (e.g. with use of forced air or a vacuum) or liquids.

Figure 4:
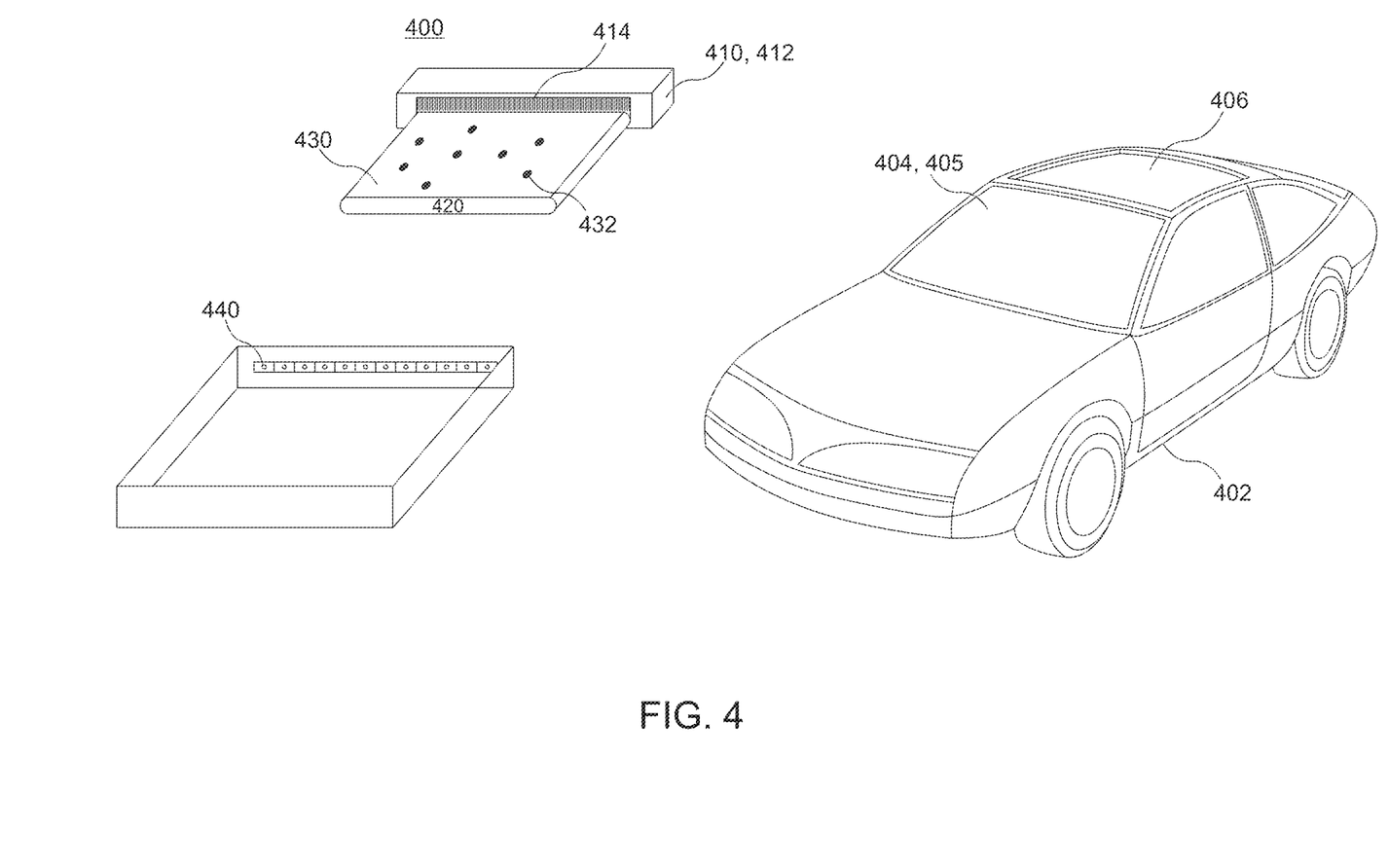
FIG. 4 shows a view of an embodiment of the air purification apparatus within a vehicle.

FIG. 4 shows a vehicle 402 comprising a sunshade 400 for purifying air 405 of an interior space 404 of a vehicle that oxidizes a plurality of pollutant compounds 407 suspended in the air. The sunshade may comprise a substrate material 420 having a photocatalytic layer 430 disposed on an at least one surface of the substrate material 420, wherein the photocatalytic layer 430 comprises a plurality of photocatalyst particles 432 and wherein a light source 440 activates the photocatalytic particles 432 to promote a reaction between the pollutant compounds 407 and the air 405 of the interior space 404 of the vehicle 402.

A vehicle 402 may be land-, sea-, or air-based. It may include any apparatus used for transportation. Additionally, the sunshade 400 is vehicle 402 independent and may be deployed in environments and systems not used or designed for transportation, such as in a home, a retail environment, public spaces, an office or any of the climate systems that operate in those spaces.

A sunshade 400 is any object or structure that is used as protection from sunlight. In a vehicle 402, it is typically used as a covering for windows such as a covering for a sunroof 406. In a further, embodiment, the sunshade 400 may further comprise a cleansing retractor 410 affixed to the sunshade 400, wherein the sunshade 400 retractable into a housing 412, wherein as the sunshade is retracted into the housing brushes 414 adjacent to the photocatalytic layer 430 disposed on the at least one surface of the substrate material 420. The sunshade 400 may be cleansed by brushing or removing materials from the photocatalytic layer 430. In place of brushes can be any apparatus for frictionally removing oxidized particles from the sunshade 400, including scrubbers, squeegees, or other tools with a flat blade, sponges, and microfiber cloths. Retracting the sunshade 400 when the window or sunroof is open may protect the substrate material 420 from being touched or exposed to dirt and pollutants coming from outside the vehicle.

The vehicle 402 may comprise a light source 440 consisting of LEDs located exterior to the substrate material 420. For example, in a vehicle 402, the light source 440 may be located on the exterior side of a substrate material 420 between the sunroof glass 406 and the substrate material 420. The light source 440 would then be shining into the air cavity between the sunroof glass 406 and the photocatalytic layer 430 of the substrate material 420. This would protect any inhabitants of the vehicle from being exposed to UV radiation while still activating the photocatalytic layer 430 of the substrate material 420. Furthermore, the light source 440 could be positioned or directed to reflect UV light off the sunroof glass 406. This would enable the sunroof glass 406 to be used to refract or guide light across the entire surface of the photocatalytic layer 430. Optionally, the sunroof glass 406 can be coated with a UV or light-reflective coating or film. This film would aid with the refraction of the light on the glass as well as protect those outside the vehicle from the UV radiation.

Any of the above-described embodiments may be combined with any other embodiment (or combination of examples) unless explicitly stated otherwise. The foregoing description of one or more implementations provides illustration and description but is not intended to be exhaustive or to limit the scope of embodiments to the precise form disclosed. Modifications and variations are possible in light of the above teachings or may be acquired from practice of various embodiments.

The aspects and features mentioned and described together with one or more of the previously detailed embodiments and figures, may as well be combined with one or more of the other examples to replace a like feature of the other embodiment or to additionally introduce the feature to the other embodiment.

Examples may further be or relate to a computer program having a program code for performing one or more of the above methods, when the computer program is executed on a computer or processor. Steps, operations or processes of various above-described methods may be performed by programmed computers or processors. Examples may also cover program storage devices such as digital data storage media, which are machine, processor, or computer-readable and encode machine-executable, processor-executable, or computer-executable programs of instructions. The instructions perform or cause performing some or all of the acts of the above-described methods. The program storage devices may comprise or be, for instance, digital memories, magnetic storage media such as magnetic disks and magnetic tapes, hard drives, or optically readable digital data storage media. Further embodiments may also cover computers, processors or control units programmed to perform the acts of the above-described methods or (field) programmable logic arrays ((F)PLAs) or (field) programmable gate arrays ((F)PGAs), programmed to perform the acts of the above-described methods.

The description and drawings merely illustrate the principles of the disclosure. Furthermore, all examples and embodiments recited herein are principally intended expressly to be only for illustrative purposes to aid the reader in understanding the principles of the disclosure and the concepts contributed by the inventor(s) to furthering the art. All statements herein reciting principles, aspects, and examples of the disclosure, as well as specific examples thereof, are intended to encompass equivalents thereof.

A functional block denoted as "means for . . . " performing a certain function may refer to a circuit that is configured to perform a certain function. Hence, a "means for s.th." may be implemented as a "means configured to or suited for s.th.", such as a device or a circuit configured to or suited for the respective task.

Functions of various elements shown in the figures, including any functional blocks labeled as "means", "means for providing a signal", "means for generating a signal.", may be implemented in the form of dedicated hardware, such as "a signal provider", "a signal processing unit", "a processor", "a controller", as well as hardware capable of executing software in association with appropriate software. When provided by a processor, the functions may be provided by a single dedicated processor, by a single shared processor, or by a plurality of individual processors, some of which or all of which may be shared. However, the term "processor" or "controller" is by far not limited to hardware exclusively capable of executing software but may include digital signal processor (DSP) hardware, network processor, application specific integrated circuit (ASIC), FPGA, read only memory (ROM) for storing software, random access memory (RAM), and non-volatile storage. Other hardware, conventional and/or custom, may also be included.

A block diagram may, for instance, illustrate a high-level circuit diagram implementing the principles of the disclosure. Similarly, a flow chart, a flow diagram, a state transition diagram, a pseudo code, and the like may represent various processes, operations, or steps, which may, for instance, be substantially represented in a computer-readable medium and so executed by a computer or processor, whether or not such computer or processor is explicitly shown. Methods disclosed in the specification or the claims may be implemented by a device having means for performing each of the respective acts of these methods.

It is to be understood that the disclosure of multiple acts, processes, operations, steps, or functions disclosed in the specification or claims might not be construed as to be within the specific order, unless explicitly or implicitly stated otherwise, for instance for technical reasons. Therefore, the disclosure of multiple acts or functions will not limit these to a particular order unless such acts or functions are not interchangeable for technical reasons. Furthermore, in some examples/embodiments a single act, function, process, operation, or step may include or may be broken into multiple sub-acts, -functions, -processes, -operations, or -steps, respectively. Such sub acts may be included and part of the disclosure of this single act unless explicitly excluded.

Furthermore, the following claims are hereby incorporated into the detailed description, where each claim may stand on its own as a separate example/embodiment. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to include also features of a claim to any other independent claim even if this claim is not directly made dependent to the independent claim

What is claimed is:

1. A method for purifying air of an interior space of a vehicle by oxidizing a plurality of pollutant compounds suspended in the air, the method comprising:
   exposing the air of the interior space to a photocatalytic layer,
      wherein the photocatalytic layer is disposed onto an at least one surface of a porous substrate material located in the interior space,
      wherein the photocatalytic layer comprises a plurality of photocatalyst particles,
   determining occupancy information on the interior space, and
   activating the photocatalytic layer with emissions of an artificial light source based on the occupancy information,
      wherein the activated photocatalyst particles react with water in the air to create hydroxyl radicals,
      wherein the hydroxyl radicals oxidize the plurality of pollutant compounds, and cleansing the photocatalytic layer, wherein cleansing comprises agitating the photocatalytic layer to remove the plurality of oxidized pollutant compounds when the occupancy information determines an absence of an occupant.

2. The method of claim 1, wherein the photocatalytic layer is non-reactive with the substrate material.

3. The method of claim 1, wherein the photocatalytic layer comprises a semiconductor material configured to cause a photoelectrochemical reaction.

4. The method of claim 1, further comprising suspending the substrate material in the interior space.

5. The method of claim 1, wherein the porous substrate material includes at least one of the group of:
   a woven fabric; and
   a non-woven fabric.

6. The method of claim 1, wherein the porous substrate material includes at least one of the group of:
   a ceramic;
   a metal;
   a polymer, or
   a natural fiber.

7. The method of claim 1, wherein the artificial light source's emissions consist essentially of far-UV-C light when the occupancy information determines a presence of an occupant.

8. The method of claim 1, wherein the artificial light source's emissions consist essentially of UV-C light when the occupancy information determines an absence of an occupant.

9. The method of claim 1, further comprising inducing airflow in the interior space during the cleansing.

10. The method of claim 9, wherein inducing airflow comprising forcing airflow using at least one of the group of:
    a fan; and
    an HVAC system.

11. The method of claim 1, wherein the substrate material comprises at least one of the group of:
    an interior panel of the vehicle,
    a seat cover,
    a sunshade,
    a sunroof shade;
    a parcel shelf;
    a trunk cover.

12. An apparatus for purifying air of an interior space of a vehicle by oxidizing a plurality of pollutant compounds suspended in the air, the apparatus comprising:

an occupancy sensor,
an artificial light source producing emissions consisting essentially of UV-C light,
a substrate material having a photocatalytic layer disposed on an at least one surface of the substrate material, and
an agitator for cleansing the photocatalytic layer,
    wherein the photocatalytic layer comprises a plurality of photocatalyst particles;
    wherein the emissions of the artificial light source activate the photocatalyst particles when the occupancy sensor determines an absence of an occupant;
    wherein the activated photocatalyst particles react with water in the air to create hydroxyl radicals;
    wherein the hydroxyl radicals oxidize the plurality of pollutant compounds; and
    wherein the photocatalytic layer is cleansed by removing the plurality oxidized pollutant compounds with the agitator when the occupancy sensor determines an absence of an occupant.

13. A sunshade apparatus for purifying air of an interior space of a vehicle that oxidizes a plurality of pollutant compounds suspended in the air, the sunshade apparatus comprising:
an occupancy sensor,
an artificial light source producing emissions consisting essentially of UV-C light,
a shade comprising a substrate material having a photocatalytic layer disposed on an at least an upper surface of the substrate material,
    wherein the photocatalytic layer comprises a plurality of photocatalyst particles;
    wherein the emissions of the artificial light source are directed at the upper surface of the substrate material to activate the photocatalyst particles when the shade is closed and when the occupancy sensor determines an absence of an occupant;
    wherein the activated photocatalyst particles react with water in the air to create hydroxyl radicals,
    wherein the hydroxyl radicals oxidize the plurality of pollutant compounds, and
an agitator for cleansing the photocatalytic layer of the shade,
    wherein the photocatalytic layer is cleansed by removing the plurality oxidized pollutant compounds with the agitator when the occupancy sensor determines an absence of an occupant.

14. The method of claim 1, wherein determining the occupancy of a vehicle comprises using at least one of the group of:
a seat sensor;
a camera,
a steering wheel hand detector,
a door sensor, or
a motion sensor.

15. The method of claim 1, further comprising controlling an ambient light source to indicate the activation of the photocatalytic layer.

16. The method of claim 8, further comprising sensing a level of UV light in the interior space and adjusting an intensity of the artificial light based on the level of UV light.

* * * * *